May 23, 1972 L. H. SHOESMITH Plant Pat. 3,195

CHRYSANTHEMUM PLANT (ELDORADO)

Filed Oct. 5, 1970

INVENTOR.
LEONARD H. SHOESMITH

BY Rummler & Snow
Attys.

United States Patent Office

Plant Pat. 3,195
Patented May 23, 1972

3,195

CHRYSANTHEMUM PLANT (ELDORADO)

Leonard H. Shoesmith, Westfield-Woking, Surrey, England, assignor to Pan-American Plant Company, West Chicago, Ill.

Filed Oct. 5, 1970, Ser. No. 78,314
Int. Cl. A01h *5/00*
U.S. Cl. Plt.—78 1 Claim

ABSTRACT OF THE DISCLOSURE

A new variety of standard chrysanthemum plant having very large yellow blooms of the semi-incurved type produced on long strong stems, distinguished by its uniform response and capability of being flowered the year-around under greenhouse culture, and by its resistance to Botrytis.

BACKGROUND OF THE NEW PLANT

This new variety of chrysanthemum plant was discovered by me in the course of extensive breeding efforts carried on by me since 1967 at West Chicago, Ill., with the object of developing improved varieties of chrysanthemums having distinctive form and color, as well as improved growth habits. This plant originated as a seedling resulting from random crosses of commercial varieties of standard greenhouse plants and was selected for propagation and test because of its apparent growth vigor, its long strong stems, and its bright yellow blooms of very large size.

I have propagated this new plant, at West Chicago, Ill., by vegetative cuttings, and trial under greenhouse culture showed the new plant to have the additional advantages of uniform photo-period response and ability to be flowered at any desired time of the year. Asexual propagation of tis new plant at West Chicago, Ill., and at Cortez, Fla., has shown conclusively that all of the before mentioned advantages and characteristics come true from generation to generation and are firmly fixed.

DESCRIPTION OF THE DRAWINGS

My new variety of chysanthemum plant is illustrated by the accompanying drawing, in which the principal figure shows the bloom in full color, as nearly true as it is reasonably possible to obtain by conventional photographic reproduction processes, and the ink drawn figures show the configuration of typical specimens of the leaves.

DESCRIPTION OF THE PLANT

Figure 1:
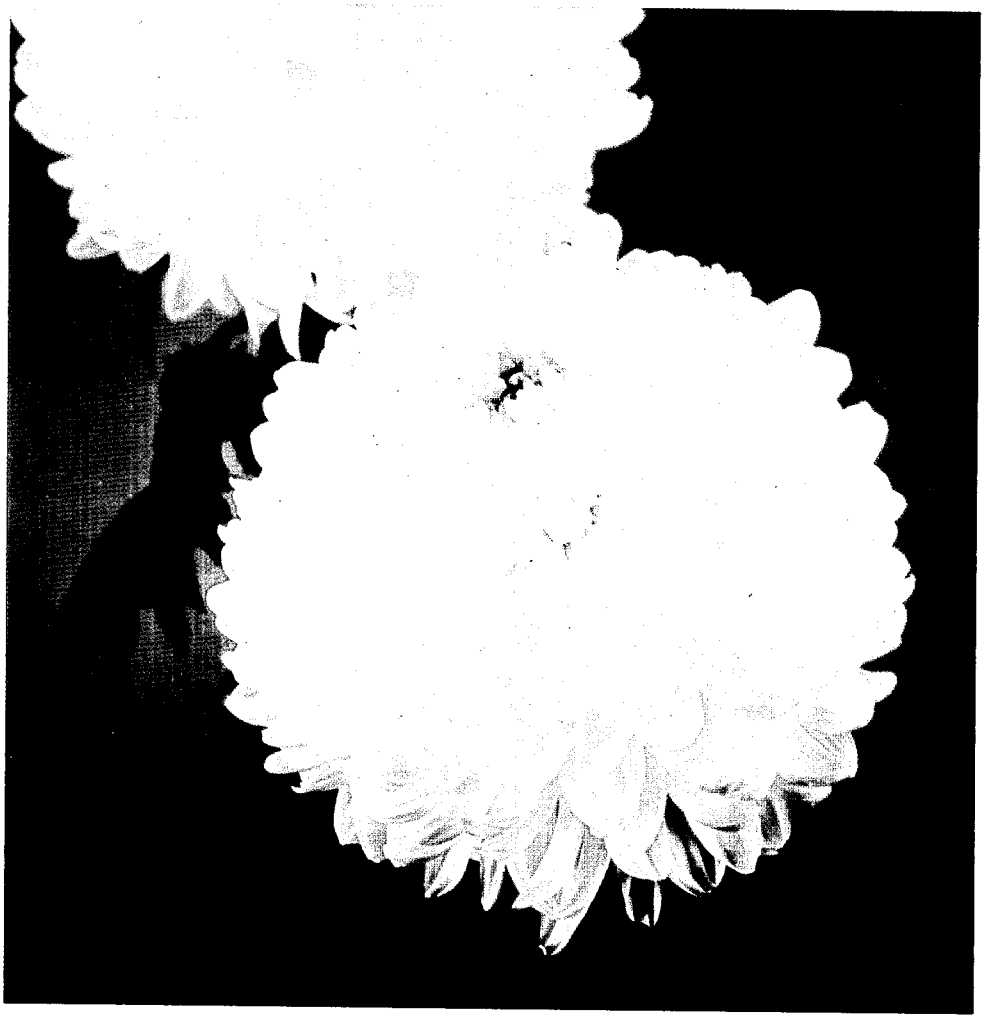
Figure 2:
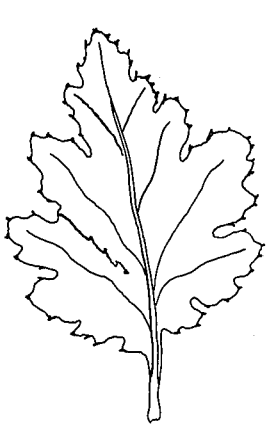
Figure 3:
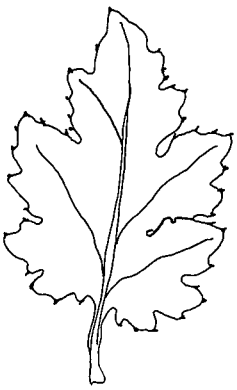

The following is a detailed description of the new variety of chrysanthemum plant with color designations according to the Horticultural Colour Chart issued by The British Colour Council.

*The plant*

Origin: Seedling—selected from random crosses.
Parentage: Unknown.
Classification:
- Botanic.—*Chrysanthemum morifolium.*
- Commercial.—Standard semi-incurved.

Form: Bush—grown as a single stem standard.
Height: Tall—three feet.
Growth: Terminal. Vigorous, strong and sturdy, upright and branching.
Foliage: Quantity—sparse, with about 16 leaves on 3 feet of stem length.
- *Leaf size.*—Approximately 6 inches long x 4 inches wide.
- *Shape.*—Lanceolate, lobed and serrated.
- *Texture.*—Leathery.
- *Color.*—Upper side—Spinach Green 0960. Under side—Spinach Green 0960/2.
- *Petioles.*—¾ inch long.

*Ribs and veins.*—Prominent, alternate and pinate.

*The bud*

Form: Round and ovoid.
Diameter: One inch.
Depth: ¼ inch.
Opening rate: Slowly—3 weeks.
Color:
- *When petals first divide.*—Green.
- *When sepals begin to unfurl.*—Yellow.

Sepals: Stand up.
Calyx:
- *Shape.*—Flat-disc.
- *Size.*—Large—one inch diameter.

Peduncle: 2½ inches long, smooth and erect. Color: Green.

*The flower*

Blooming characteristic: Photoperiod responsive for year-around culture.
Response: Consistent nine week response.
Natural season: Late October.
Size: Very large—5½ inch diameter and 3½ inches deep (disbudded).
Borne: Singly upon disbudding—otherwise as raceme cluster.
Shape: Flat with low center when bloom first opens. Shape does not change with maturity.
Petalage: Many in number, in composite arrangement.
- *Form.*—Ray florets—2½ to 3 inches long.
- *Color.*—Outer petal—Sulfur Yellow ½. Inside petal—Sulfur Yellow ½. Reverse side—Sulfur Yellow ½.

Peduncle: Sturdy and upright, 2½ inches long and ¼ inch in diameter. Color: Green.
Texture: Soft with satiny appearance.
Discoloration: None—color holds.
Persistence: Hangs on and dries.
Lasting quality: Long lasting on plant and as a cut flower.

*Reproductive organs*

Stamens:
- *Anthers.*—One per disc floret, ⅛ inch long and in composite arrangement.
- *Filaments.*—Length—⅛ inch. Color—Green.

Pollen: Color—Indian Yellow 6.
Pistils: One per ray floret—¼ inch long.
Stigmas: Color—Pale Green.

*Fruit*

Fertile seeds of oblong shape and brown color at maturity.

The principal distinctions of my new variety of *Chrysanthemum morifolium* reside in its capability of uniform nine week response with a strong, clean and erect growth habit, the intense color of its blooms and the absence of neckiness, and the ability to be flowered at any selected period, the year-around, for greenhouse culture as a standard plant. This new plant is a vigorous grower during high light period, does not sunburn, and appears to resist Botrytis.

I claim:

1. A new and distinct variety of chrysanthemum plant of the standard semi-incurved type, substantially as herein shown and described, characterized by the intense yellow color and the very large size of its bloom, its vigorous growth and its consistent nine week response with strong, upright habit, and its capability of being flowered at any time of the year.

No references cited.

ROBERT E. BAGWILL, Primary Examiner